United States Patent
Meyer

(10) Patent No.: US 6,308,098 B1
(45) Date of Patent: Oct. 23, 2001

(54) PROCESS FOR DETECTION OF PHYSICAL POSITION OF A HUMAN BEING

(75) Inventor: Wolfgang Meyer, Erlangen (DE)

(73) Assignee: Biotronik Mess-und Therapiegerate GmbH & Co. Ingenieurburo Berlin, Berlin (DE)

( * ) Notice: Subject to any disclaimer, the term of this patent is extended or adjusted under 35 U.S.C. 154(b) by 0 days.

(21) Appl. No.: 09/391,857

(22) Filed: Sep. 8, 1999

(30) Foreign Application Priority Data

Sep. 8, 1998 (DE) .............................................. 198 42 107

(51) Int. Cl.$^7$ .................................................... A61N 1/365
(52) U.S. Cl. .............................................. 607/17; 600/547
(58) Field of Search ................................. 607/9, 17, 19, 607/20, 23, 24, 26; 600/547, 595

(56) References Cited

U.S. PATENT DOCUMENTS

| 4,428,378 | * | 1/1984 | Anderson et al. ...................... 607/17 |
| 4,896,068 | | 1/1990 | Nilsson . |
| 4,926,863 | | 5/1990 | Alt . |
| 5,215,084 | | 6/1993 | Schaldach . |
| 5,336,243 | | 8/1994 | Schaldach . |
| 5,354,317 | | 10/1994 | Alt . |
| 5,466,245 | | 11/1995 | Spinelli et al. . |
| 5,676,690 | | 10/1997 | Norén . |
| 5,797,840 | | 8/1998 | Akselrod et al. . |
| 5,836,889 | | 11/1998 | Wyborny et al. . |

FOREIGN PATENT DOCUMENTS

| 39 23 801 A1 | 1/1991 | (DE) . |
| 196 09 411 A1 | 9/1997 | (DE) . |
| 0 845 240 A1 | 6/1998 | (EP) . |
| 0 911 063 A1 | 4/1999 | (EP) . |
| WO 91/08017 | 6/1991 | (WO) . |

OTHER PUBLICATIONS

S. Akselrod et al., "Hemodynamic Regulation: Investigation by Spectral Analysis" Am. J. Physiol. 1985, H867–H875.

* cited by examiner

Primary Examiner—George R. Evanisko
(74) Attorney, Agent, or Firm—Christie, Parker & Hale, LLP

(57) ABSTRACT

A process for detecting the physical positions or changes of position of a human being based on detecting a physiological signal dependent on a sympathetic/parasympathetic nerve system in each case in the heart or in a vessel near the heart by means of a sensor at pre-specified times, in particular, based in each case on a physiological or stimulation event, deriving a value of a signal parameter in each case, from this signal according to a pre-specified signal processing rule and stored determining a fluctuation curve of the stored signal parameter values, performing a frequency analysis of the fluctuation curve to obtain the spectral power density evaluating the spectral power density, resulting in the issuance of a position signal as a function of the evaluation result, whereby the morphology of the signals is detected and the value of the signal parameter is, in each case, derived from morphology of an individual detected signal.

20 Claims, 2 Drawing Sheets

PROCESS FOR DETECTION OF PHYSICAL POSITION OF A HUMAN BEING

FIELD OF THE INVENTION

The invention concerns a process for the detection of the physical positions of a human being by evaluating the morphology of individual signals detected from a sympathetic/parasympathetic nerve system and the relationship of their spectral power densities, as well as an apparatus for performance of this process and an implantable cardiotherapy device containing such an apparatus.

BACKGROUND OF THE INVENTION

Rate-adaptive cardiac pacemakers are known which control the adaptive stimulation rate by the use of a comparison between the current sensor signal morphology and the morphology determined in the resting patient. Thus, for example, in the case of the "Inos" pacemaker of the applicant the respective current intracardial impedance curve is compared with a reference curve and the adaptive rate is determined from the integral difference. In the case of such pacemakers, it is important to keep the reference curve constantly current on the one hand, but on the other hand to only actually update it in the resting patient. For such an automatic updating of the reference curve, detection of the physical positions (standing or sitting or lying down) of the patient is desirable, since, within certain limits, the position detection also enables the detection of resting phases of the patient.

With rate-adaptive cardiac pacemakers, an additional problem may exist in that the signal morphology of a measured signal used for the rate adaptation exhibits great changes when the patient changes positions without the cause being capable of detection by a rate adaptation algorithm. This can result in paradoxical pacemaker behavior, such as a counterproductive drop in the stimulation rate when the patient stands up. A means of independent position detection would be of great utility, so that the rate adaptation algorithm could receive an additional input signal in order to be able to react properly to changes in position.

Of no less importance, is a determination of the proper time for an automatic night reduction in the stimulation rate by setting the time basis of the pacemaker independent of the influence of time zone changes or changing daily rhythm of the patient using the patient's actual lying down and resting phases; cf. PCT International Publication No. W091/08017.

Proposals have long been known to detect the physical position of patients using mercury or similar position-sensitive switches. However, because of various problems, to date, these have not proven to be effective in practice. In basic research, the heart rate variability in predefined low frequency (LF) intervals (0.05–0.15 Hz) and high frequency (HF) intervals (0.15–0.4 Hz) is used as an indicator of sympathovagal equilibrium which is affected by a change in position; cf. S. Akselrod et al. in "Hemodynamic Regulation: Investigation by Spectral Analysis", Am. J. Physiol., 249, H 867–875 (1985). The process is not applicable in the particularly important and practical area of pacemaker patients since the variability of the heart rate in pacemaker patients is usually not available.

OBJECTS AND SUMMARY OF THE INVENTION

Consequently, the principal object of the invention is to report a reliable process, also suitable for pacemaker patients, for position detection of a human being and an apparatus for performance of this process.

The principal object of the present invention more specifically, relies on the relationship of spectral power densities in both the HF and the LF internals.

The invention includes the basic teaching of describing a process for position detection, termed orthostasis, a change between standing and lying, using the morphology of intracardial physiological sensor signals. The sensor signals which are dependent on sympathetic/parasympathetic nerve systems, are suitable for the purposes of the invention. In particular, hemodynamic signals, such as impedance or pressure, and electrical signals such as ventricular evoked response (VER) signals may also be used.

The process of the present invention extracts a specific signal parameter from the signal morphology of an individual heart cycle. This signal parameter is determined for a large number of heart cycles, and its beat by beat fluctuations are determined. The beat by beat fluctuations are subjected to a frequency analysis to obtain a spectral power density. The spectral power density represents a measure of the beat by beat variability of the signal parameter with specific variation frequencies. A high power density at a specific frequency indicates a high variability with this same variation frequency. In a standing patient, the relationship between high (between approximately 0.15 and 0.4 Hz) and low (between about 0.05 and 0.15 Hz) variation frequencies of signals under sympathetic/parasympathetic influence is low; in contrast, in a reclining patient, this relationship is high. Consequently, the spectral power density is, in each case, integrated over the high frequency range and the low frequency range in order to be able to determine the position of the patient from beat to beat from the relationship of the two intervals.

In a preferred embodiment, the beat by beat variability of the intracardial impedance signal is used for detection of position changes of a patient. For measurement of an impedance signal, preferably a high frequency alternating current pulse with an average current strength of 1.3 mA is fed in via a unipolar pacemaker electrode, and a voltage drop between an electrode point and a pacemaker housing is measured.

The slope of the impedance signal at a fixed point during a heart cycle is determined as a suitable parameter to construct the time series from a signal curve. Analogously to the above-mentioned analysis of heart rate variability, time-dependent frequency analyses of a time series of a slope parameter extracted from the impedance curve are performed, in particular. In order to investigate an entire frequency spectrum with time resolution, autoregressive spectral analysis is used (ARSA). A linear model is fitted to the measured time series of a parameter and the spectral power density is calculated from the coefficients. This occurs preferably at each point of the time series with an autoregressive model of order 20. The calculated spectral power density is in each case integrated into the subdomains of lower frequencies (LF—blood pressure variability) and higher frequencies (HF—breath variability) and subsequently compared.

BRIEF DESCRIPTION OF THE DRAWINGS

Advantageous refinements of the invention are presented in greater detail in the detailed description of the invention, along with the description of the preferred embodiment of the invention with reference to the Figures. They depict.

DETAILED DESCRIPTION OF THE INVENTION

Figure 1:
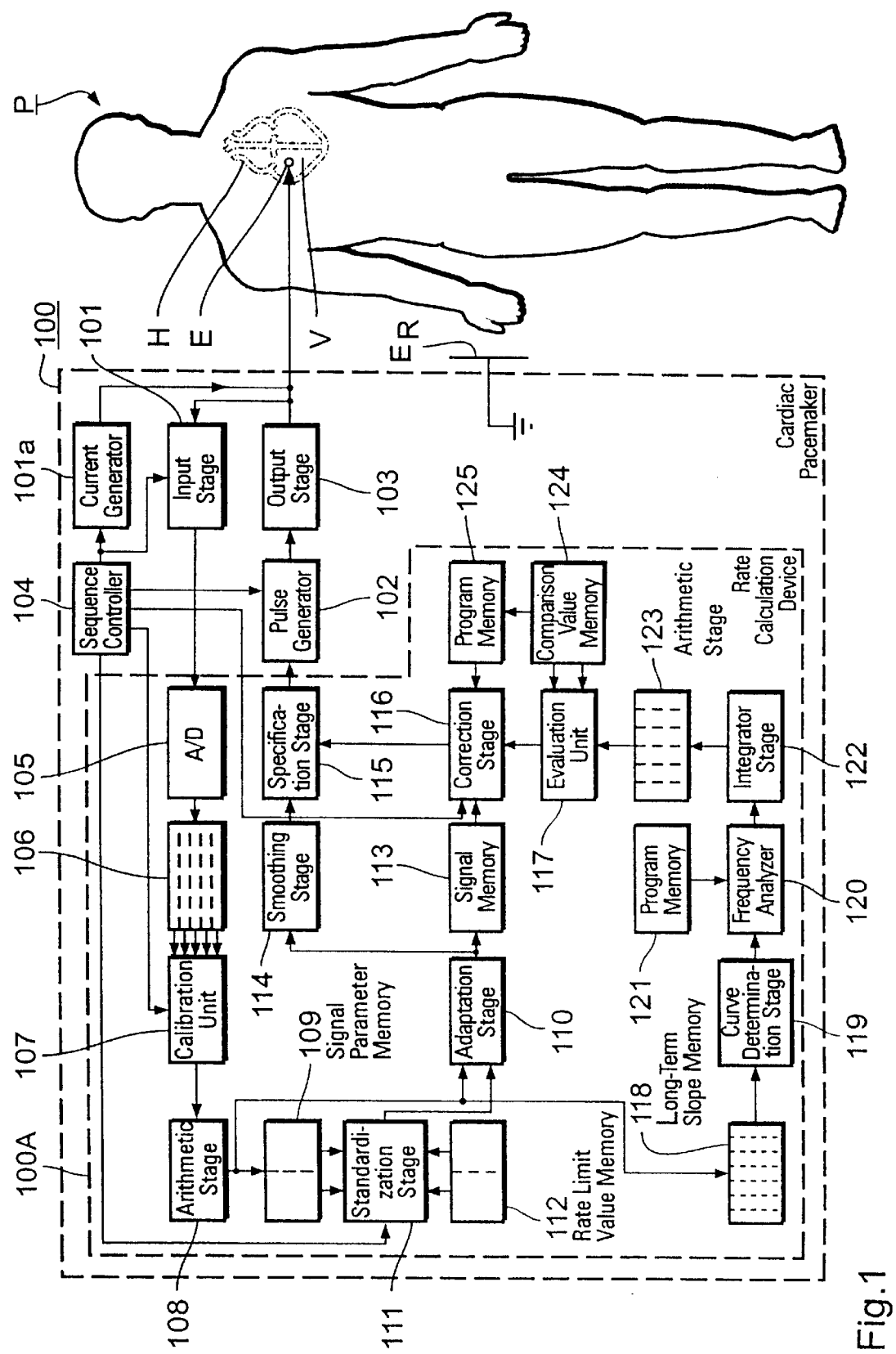
FIG. 1 a functional block diagram of a rate-adaptive cardiac pacemaker as a preferred exemplary embodiment of the invention, and FIG. 2 a graphic depiction to explain the significance of the results obtained with the process according to the invention.

In FIG. 1, essential components of a rate-adaptive cardiac pacemaker 100 are depicted in the form of a functional block diagram, whereby, in the interest of clarity, known pacemaker elements not essential to the performance of the invention are omitted.

The cardiac pacemaker 100 is connected on the input side and also on the output side with an intracardial electrode E in a ventricle V of a heart H of a patient. In addition to a heart signal input stage for the detection of ventricular heart signals (known and not depicted here), an impedance stage is connected with the electrode E. This includes a scanning current generator 101a and an impedance signal input stage 101, which has filter and amplification stages for the signal-shape faithful detection of an intracardial impedance signal. Stimulation pulses generated by a stimulation pulse generator 102 are sent via an output stage 103 and the electrode E to the ventricle V. A housing electrode $E_R$ serves as a reference electrode for unipolar signal detection and stimulation.

The pacemaker 100 includes a sequence controller 104, which controls the entire operating cycle, however, in the FIG. 1, in the interest of clarity, only the control signal connections to a few components important in the present connection are depicted. In connection with the invention, it is important that the sequence controller 104 controls the scanning current generator 101a as well as the input processing of a time-dependent impedance signal in a pre-specified time window after stimulus by the impedance signal input stage 101 in temporal coordination with the output of the stimulation pulse.

Generation and supply of the rate control signals for control of the stimulation rate according to the physiological need of the patient P take place in a rate calculation device 100A connected on the input side with the impedance signal input stage 101 and on the output side with the stimulation pulse generator 102. This includes an impedance signal memory unit 106 connected via an A/D converter 105 with the impedance signal input stage 101 with a plurality of separate memory areas, in which, in each case a complete impedance signal is stored following a stimulus. A calibration unit 107 is connected with the memory unit 106 in a likewise manner controlled by the sequence controller 104.

In the calibration unit 107, once or at predefined intervals, those "points in time" (time intervals to the stimulus time) of the impedance signals for which the difference in signal amplitude presents maximum variability are determined for a predefined period of time or a predefined number of impedance signals (corresponding to a program stored in the sequence controller 104). In an arithmetic stage 108 connected downstream from the calibration unit 107, the current quotient of the amplitude difference value $\Delta Z = Z_2(t_2) - Z_1(t_1)$ is determined continuously for the respective last impedance signal picked up Z(t) at these points in time, and a difference $(t_2-t_1)$ of the points in time is calculated, i.e., the slope of the impedance curve in the section of highest variability is determined.

The arithmetic stage 108 is connected on the output side with a signal parameter memory 109 as well as an adaptation stage 110. The respective largest and smallest slope values detected are held in the memory 109, continuously updated according to a first-in first-out (FIFO) principle, and these are fed to an input pair of a standardization stage 111, which is connected via a second input pair with a rate limit value memory 112, in which minimum and maximum admissible stimulation rate values for the rate control are stored.

In the standardization stage 111, the currently valid "physiological" curve of the signal parameter is determined from the respective minimum and maximum amplitude difference value present and predefined minimum and maximum stimulation rate values in correlation with the stimulation rate and fed to the adaptation stage 110. In the latter, the current primary rate control signal is calculated from this and from the current value of the slope obtained from the arithmetic stage 108.

The adaptation stage 110 is connected on the output side in parallel with a rate control signal memory 113 as well as a smoothing stage 114. The smoothing stage 114, in which a reprocessing of the rate control signal to prevent excessively large "rate jumps" is performed, is connected with an input of a rate specification stage 115, in which a valid rate control signal is developed.

The rate control signal memory 113 is connected with an input of a correction stage 116, which is connected via a second input with a comparator and evaluation unit 117, which provides a position signal serving as a correction signal for the primary rate control signal, obtained as described in the following section.

A long-term slope memory 118, in which (again according to the FIFO principle) the slope values from a large number of impedance measurements are stored, is also connected to the output of the arithmetic stage 108. A fluctuation curve determination stage 119, in which the curve of the time variability of their fluctuations is determined for all currently stored slope signals, is connected to this. A frequency analyzer 120 for determination of the spectral power density of the fluctuation curve using a linear model of the so-called autoregressive spectral analysis (ARSA) stored in a frequency analysis program memory 121 is connected downstream from this. An integrator stage 122 for integration of the frequency components within the two permanently programmed ranges of 0.05 to 0.15 Hz ("LF") and 0.15 to 0.4 Hz ("HF") is connected to the output of the frequency analyzer 120. An additional arithmetic stage 123 to develop the quotient of the two current integral values is connected to the output of the integrator stage 121. The output of the arithmetic stage 123 is sent to a data input of the comparator and evaluation unit 117, which is connected via an additional input with a re-programmable comparison value memory 124 and in which an evaluation of the current quotient takes place using comparison values. And finally, the comparator and evaluation unit 117 issues a position signal indicating the position of the patient (standing/sitting/lying down) to the correction stage 113 which is calculated there for determination of a secondary rate control signal according to a correction rule stored in a correction program memory 125.

Figure 2:
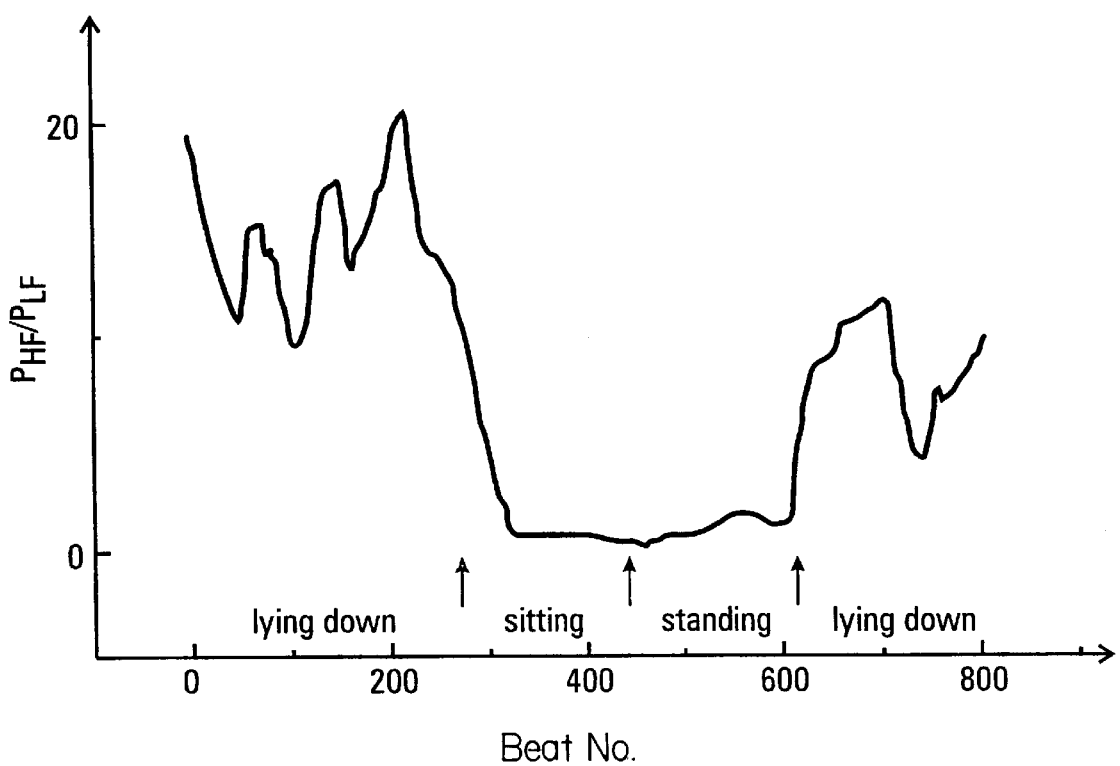

FIG. 2 illustrates, in the form of a time curve, experimentally determined from several hundred heart beats, the dependency of the quotient of the spectral power density $P_{HF}/P_{LF}$ calculated in the arithmetic stage 122 on the position of the patient and thus the relevance of this variable for obtaining a correction signal for the rate adaptation of a pacemaker.

The invention is not limited in its embodiment to the above described preferred exemplary embodiment. Rather, a number of variants are possible, which make use of the solution presented even in other types of embodiments.

The detection of the physiological variables, from which the relevant signal parameter is determined, does not necessarily take place by electric means via one or a plurality of electrode(s), but may even occur mechanically, perhaps by means of a pressure sensor placed in the heart or in a vessel near the heart.

Besides the ARSA process, the spectral energy density may also be determined with a different known correlation or transformation process.

The evaluation of the spectral energy density does not necessarily require development of a relationship from two ranges, but may consider more ranges or only extend to one frequency range.

What is claimed is:

1. A process for detecting physical positions or changes of position of a human being, comprising:

detecting a plurality of physiological signals dependent on a sympathetic/parasympathetic nerve system in a heart of a human being or in a vessel near the heart of the human being by a sensor at pre-specified times, each of said pre-specified times corresponding to a physiological or a stimulation event;

deriving and storing a plurality of values as signal parameters from the plurality of physiological signals according to a pre-specified signal processing rule;

determining a fluctuation curve of the stored signal parameter values;

performing a frequency analysis of the fluctuation curve to obtain a spectral power density;

evaluating the spectral power density based on a pre-defined algorithm;

issuing a position signal as a function of the evaluation of the spectral power density;

wherein detecting includes detection of a morphology for each of the plurality of physiological signals and wherein deriving includes derivation of the values as signal parameters in each case from the morphology of an individually detected signal.

2. A process according to claim 1, wherein evaluating the spectral power density includes determining a relationship of the values of the spectral power density in at least two pre-specified frequency ranges and wherein issuing includes issuing the position signal as a function of the relationship determined.

3. A process according to claim 1, wherein the physiological signal is an intracardially, unipolarly detected impedance signal or a ventricular evoked response and a contractility parameter.

4. A process according to claims 1 or 2, wherein signal detection is undertaken in sync with natural or evoked heart beats and a determination of fluctuation values is undertaken on a beat by beat basis.

5. A process according to claim 1, wherein spectral power densities are integrated into pre-specified frequency ranges and a relationship is developed from integral values.

6. A process according to claim 1, wherein a relationship of spectral power densities is developed in a first range of frequencies from 0.05 to 0.15 Hz to in a second range of frequencies from 0.15 to 0.4 Hz.

7. A process according to claim 1, wherein beat by beat variability of a plurality of intracardial impedance signals is used for detecting position changes of a human being.

8. An apparatus for detecting physical positions or changes of position of a human being, comprising:

a sensor locatable in a heart of the human being or a vessel near the heart for detecting a plurality of morphologically faithful, physiological signals;

a control unit to actuate the sensor at pre-specified times, which is adapted to be connected to a physiological event detector or a stimulation signal generator;

a plurality of first processing units connected to an input side of the sensor for determining a plurality of values as signal parameters from the morphology of the signals detected according to a pre-specified signal processing rule;

signal parameter memory for storing the signal parameter values determined previously;

a second processing unit connected to an input side of the signal parameter memory for determining a fluctuation curve of the stored signal parameter values;

a frequency analyzer connected to an input side of the second processing unit for obtaining a spectral power density from the fluctuation curve;

a third processing unit connected to an input side of the frequency analyzer for determining a relationship of the values of the spectral power density in at least two pre-specified frequency ranges; and a comparator and an evaluation unit connected to an input side of the third processing unit to issue a position signal as a function of the relationship determined.

9. An apparatus according to claim 8, wherein the sensor comprises a unipolar, intracardial electrode arrangement, a filter and an amplification stage designed to detect the morphology of an intracardial EKG or impedance signal.

10. An apparatus according to claims 8 or 9, wherein the frequency analyzer is designed to perform an autoregressive spectral analysis for obtaining the spectral power density.

11. An apparatus according to claim 8, the third processing unit comprises an integrator stage and an arithmetic calculation unit connected downstream therefrom.

12. An apparatus according to claim 8, wherein the physiological signals comprise a plurality of intracardial impedance signals having beat-by-beat variability.

13. An apparatus according to claim 8, wherein the sensor comprises a plurality of electrodes.

14. Implantable cardiotherapy device for detecting physical positions or changes of position of a human being, comprising:

a sensor locatable in a heart of the human being or a vessel near the heart for detecting a plurality of morphologically faithful, physiological signals;

a control unit to actuate the sensor at pre-specified times, which is adapted to be connected to a physiological event detector or a stimulation signal generator;

a plurality of first processing units connected to an input side of the sensor for determining a plurality of values as signal parameters from the morphology of the signals detected according to a pre-specified signal processing rule;

signal parameter memory for storing the signal parameter values determined previously;

a second processing unit connected to an input side of the signal parameter memory for determining a fluctuation curve of the stored signal parameter values;

a frequency analyzer connected to an input side of the second processing unit for obtaining a spectral power density from the fluctuation curve;

a third processing unit connected to an input side of the frequency analyzer for determining a relationship of the values of the spectral power density in at least two pre-specified frequency ranges; and a comparator and an evaluation unit connected to an input side of the third processing unit to issue a position signal as a function of the relationship determined.

15. An implantable cardiotherapy device according to claim 14, designed as a rate-adaptive cardiac pacemaker, the pacemaker having a rate specification stage for calculation of a stimulation rate, the stage having one input for reception of the position signal connected with the output of the comparator and an evaluation unit and being designed for the processing of the position signal for calculation of a stimulation rate.

16. A process according to claim 1, wherein the signal parameters comprise impedance or VER signals.

17. An implantable cardiotherapy device according to claim 14, wherein the sensor comprises a unipolar, intracardial electrode arrangement, a filter and an amplification stage designed to detect the morphology of a intracardial EKG or impedance signal.

18. An implantable cardiotherapy device according to claim 14, wherein the frequency analyzer is designed to perform an autoregressive spectral analysis for obtaining the spectral power density.

19. An implantable cardiotherapy device according claim 14, wherein the third processing unit comprises an integrator stage and an arithmetic calculation unit connected downstream therefrom.

20. An implantable cardiotherapy device according to claim 14, wherein the physiological signals comprise a plurality of intracardial impedance signals having beat-by-beat variability.

* * * * *